US012611511B2

(12) United States Patent
Frost et al.

(10) Patent No.: US 12,611,511 B2
(45) Date of Patent: Apr. 28, 2026

(54) MULTI-ROWS PRONGS GRABBER

(71) Applicant: SHL MEDICAL AG, Zug (CH)

(72) Inventors: Jason Frost, Boca Raton, FL (US);
Slobodan Stefanov, Deerfield Beach,
FL (US)

(73) Assignee: SHL Medical AG, Zug (CH)

( * ) Notice: Subject to any disclaimer, the term of this
patent is extended or adjusted under 35
U.S.C. 154(b) by 441 days.

(21) Appl. No.: 15/734,288

(22) PCT Filed: Sep. 12, 2019

(86) PCT No.: PCT/EP2019/074297
§ 371 (c)(1),
(2) Date: Dec. 2, 2020

(87) PCT Pub. No.: WO2020/064336
PCT Pub. Date: Apr. 2, 2020

(65) Prior Publication Data
US 2021/0220565 A1     Jul. 22, 2021

Related U.S. Application Data

(60) Provisional application No. 62/735,307, filed on Sep.
24, 2018.

(30) Foreign Application Priority Data

Nov. 8, 2018     (EP) ..................................... 18205269

(51) Int. Cl.
A61M 5/32          (2006.01)

(52) U.S. Cl.
CPC ................................ A61M 5/3204 (2013.01)

(58) Field of Classification Search
CPC .................................................... A61M 5/3204
See application file for complete search history.

(56) References Cited

U.S. PATENT DOCUMENTS

| 5,098,400 A | 3/1992 | Crouse et al. |
| 7,771,397 B1 | 8/2010 | Olson |
| (Continued) | | |

FOREIGN PATENT DOCUMENTS

| CN | 106132462 A | 11/2016 |
| CN | 107106775 A | 8/2017 |
| (Continued) | | |

OTHER PUBLICATIONS

Fournier et al., Translation WO-2014091153 (Year: 2014).*
International Search Report and Written Opinion for Int. App. No.
PCT/EP2019/074297, mailed Dec. 11, 2019.

*Primary Examiner* — Emily L Schmidt
(74) *Attorney, Agent, or Firm* — McDonnell Boehnen
Hulbert & Berghoff LLP

(57) ABSTRACT

A needle shield remover for assembly with a cap of a
medicament delivery device is presented, having a remover
body with a proximal end and a distal end, and at least one
first shield gripping member, and at least one second shield
gripping member, where the first shield gripping member
and the second shield gripping member configured to engage
the needle shield. The first shield gripping member and the
second shield gripping member are arranged offset in rela-
tion to each other both in the longitudinal direction and
along the circumference surface of the remover body.

11 Claims, 6 Drawing Sheets

(56)          References Cited

U.S. PATENT DOCUMENTS

| | | | | |
|---|---|---|---|---|
| 2009/0054849 A1* | 2/2009 | Burnell | ............... | A61M 5/3213 |
| | | | | 604/198 |
| 2012/0150125 A1 | 6/2012 | Karlsson et al. | | |
| 2014/0343503 A1* | 11/2014 | Holmqvist | .......... | A61M 5/3204 |
| | | | | 81/3.4 |
| 2016/0144132 A1* | 5/2016 | Scanlon | .............. | A61M 5/3202 |
| | | | | 604/192 |
| 2018/0369495 A1* | 12/2018 | Stewart | ............... | A61M 5/3202 |

FOREIGN PATENT DOCUMENTS

| | | | | | |
|---|---|---|---|---|---|
| EP | 2886144 | A1 | 6/2015 | | |
| EP | 3257536 | A1 | 12/2017 | | |
| JP | 2014-530083 | A | 11/2014 | | |
| JP | 2016-540584 | A | 12/2016 | | |
| TW | 201334826 | A | 9/2013 | | |
| TW | 201815433 | A | 5/2018 | | |
| WO | 2010/146358 | A2 | 12/2010 | | |
| WO | 2013/058697 | A1 | 4/2013 | | |
| WO | WO-2014091153 | A1 * | 6/2014 | .......... | A61M 5/3202 |

* cited by examiner

160

140

150

130

10

120

81

80

82

83

30

10

MULTI-ROWS PRONGS GRABBER

CROSS REFERENCE TO RELATED APPLICATIONS

The present application is a U.S. National Phase Application pursuant to 35 U.S.C. § 371 of International Application No. PCT/EP2019/074297 filed Sep. 12, 2019, which claims priority to U.S. Provisional Patent Application No. 62/735,307 filed Sep. 24, 2018 and European Patent Application No. 18205269.6, Nov. 8, 2018. The entire disclosure contents of these applications are herewith incorporated by reference into the present application.

TECHNICAL AREA

The present disclosure relates to a needle shield remover and in particular to a needle shield remover for a needle shield of a medicament delivery device that has at least two sets of needle shield gripping members arranged offset in relation to each other.

BACKGROUND

Today's medicament delivery devices may be complex and involve many different components. The physical features of each component and the way components are assembled together has a direct effect on how these components are going to interact with each other and on the success rate of the medicament delivery device in use.

One such area is the removal of cap on the medicament delivery device to pull the needle shield away from a medicament container, wherein the needle shield is initially attached to a medicament container (e.g. syringe) to cover and protect the injection member (e.g. needle) on the medicament container. A successful needle shield removal involves two parts, namely the interaction between the cap and a needle shield remover as well as that between the needle shield remover and the needle shield. The cap needs to firmly grip the needle shield remover which in turn needs to firmly grip the needle shield in order for the user to successfully remove the needle shield by pulling the cap away from the medicament delivery device.

Currently, one example of a needle shield remover includes prongs that extend radially inward and configured to claws into the needle shield when the user pulls the cap. In order for the needle shield remover to firmly grip the needle shield during removal, it is important for the prongs to be able to extend as much radially inward as possible in order to ensure that the prongs will claws deep into the needle shield. However, allowing prongs to extend too much radially inward may risk colliding with the needle shield and preventing the entry of the needle shield into the needle shield remover during assembly. Thus, there is a need to maximise gripping force of the needle shield remover on the needle shield during removal while making sure that the prongs do not impede the assembly of the needle shield with the needle shield remover.

As for the assembly between the cap and the needle shield remover, it is important to ensure that the needle shield remover is not able to detach itself from the cap. It is equally important for the needle shield remover to not be able to rotate when assembled with the cap as the rotation may cause the needle shield to rotate which may in turn twist and damage the delivery member on the medicament container. Thus, there is a need to firmly couple the needle shield remover with the cap.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component. "Lateral" may also refer to a position to the side of a "longitudinally" elongated body.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

In view of the foregoing, a general object of the present disclosure is to provide a needle shield remover for a cap of a medicament delivery device, which needle shield remover is easier to assemble.

These and other aspects of, and advantages with, the present disclosure will become apparent from the following detailed description of the present disclosure and from the accompanying drawings.

According to a main aspect of the disclosure it is characterized by a needle shield remover for assembly with a cap of a medicament delivery device. The needle shield remover comprises a remover body having a proximal end and a distal end, at least one first shield gripping member, and at least one second shield gripping member. The first shield gripping member and the second shield gripping member configured to engage the needle shield. The first shield gripping member and the second shield gripping member are arranged offset in relation to each other both in the longitudinal direction and along the circumference surface of the remover body.

The remover body is substantially cylindrical and has a first circumference and a second circumference circling around different portions of the remover body, at least two of the first shield gripping members are distributed around the first circumference, at least two of the second shield gripping members are distributed around the second circumference.

The first and second shield gripping members are extending radially inwardly and towards the proximal end, the first and second shield gripping members are configured to engage a circumferential side surface, or the distal end of the needle shield.

The first and second shield gripping members have first openings between the remover body and first portions, the first and second shield gripping members have second openings between the remover body and second portions, the first opening is connected to the second opening, the first openings allow the first portion to flex radially outward.

According to another embodiment of the present disclosure, only one of the first shield gripping member is placed along a first line, only one of the second shield gripping member is placed along a second line.

The first and second shield gripping members have first portions extending from the remover body toward the proximal end and second portions extending radially inward from the first portions and toward the proximal end for engaging the needle shield.

According to one embodiment of the present disclosure, the second portion of the first shield gripping member has a shape different from that of the second portion of the second shield gripping member. However, in another embodiment, the second portion of the first shield gripping member is shaped substantially identical from the second portion of the second shield gripping member.

According to another embodiment of the present disclosure, the needle shield remover comprises a cap attachment structure that includes a plurality of cap fastening members extending radially outward from the remover body, wherein a cut-out exists between two neighbouring cap fastening members.

According to another object of the present disclosure, the needle shield remover comprises at least one cap attachment opening on an outer surface of the remover body to be configured to engage a remover attachment member of the cap.

BRIEF DESCRIPTION OF DRAWINGS

In the following detailed description of the present disclosure, reference will be made to the accompanying drawings, of which

DETAILED DESCRIPTION

Figure 1:
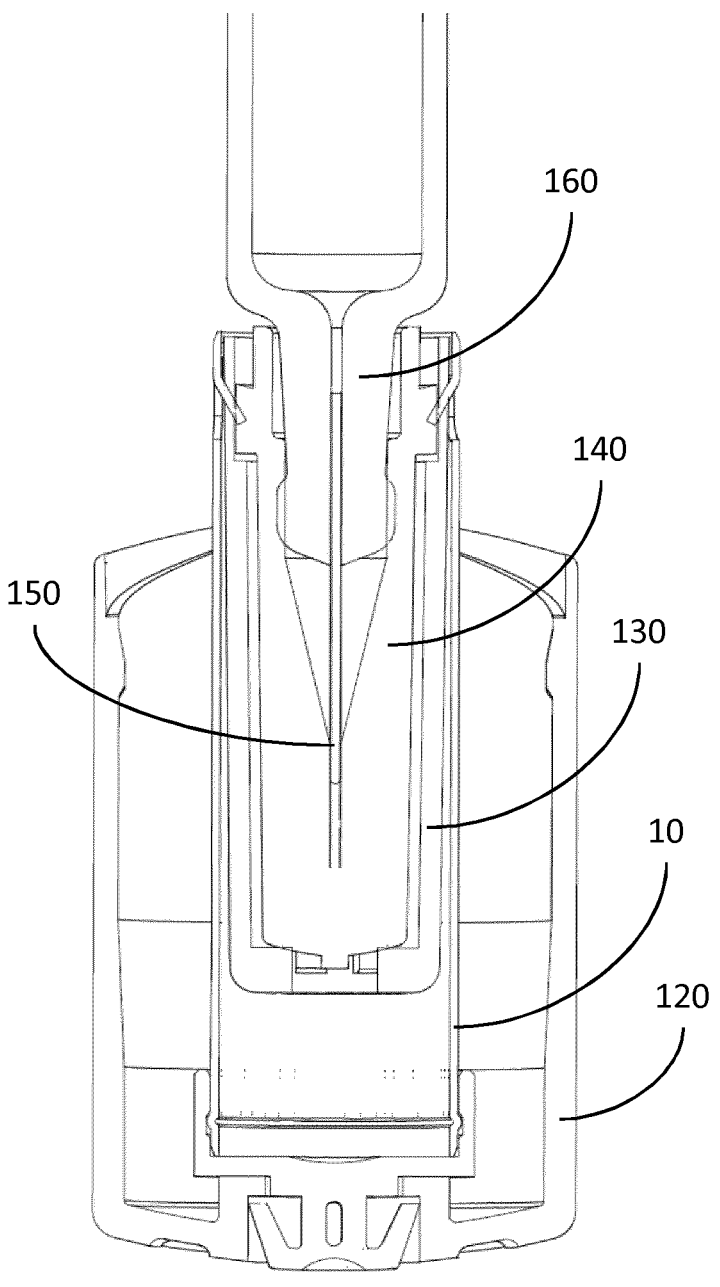
FIG. 1 shows a perspective view of a needle shield remover according to prior art.

FIG. 1 shows a known needle shield remover 10 comprised in a cap 120. The cap 120 and the needle shield remover 10 are arranged on a rigid needle shield, or RNS 130, which covers a flexible needle shield, or FNS 140. A needle 150, of a syringe 160, is embedded in the FNS 140. The syringe 160 may be housed in a medicament delivery device (not shown), for instance an auto-injector. The needle shield remover 10 is attached to the cap 120 and comprises inwardly-projecting gripping members which engage the RNS 130, either by a distal end thereof or by engagement to a circumferential surface of the RNS 130, such that removal of the cap 120 pulls the RNS 130 and the FNS 140 away from the syringe to expose the needle 150.

The present disclosure relates to a needle shield remover which is intended to be applied to known needle shields, for instance needle shields as shown in FIG. 1. The needle shield remover of the present disclosure is described in more detail in conjunction with FIGS. 2-6.

Figure 2:
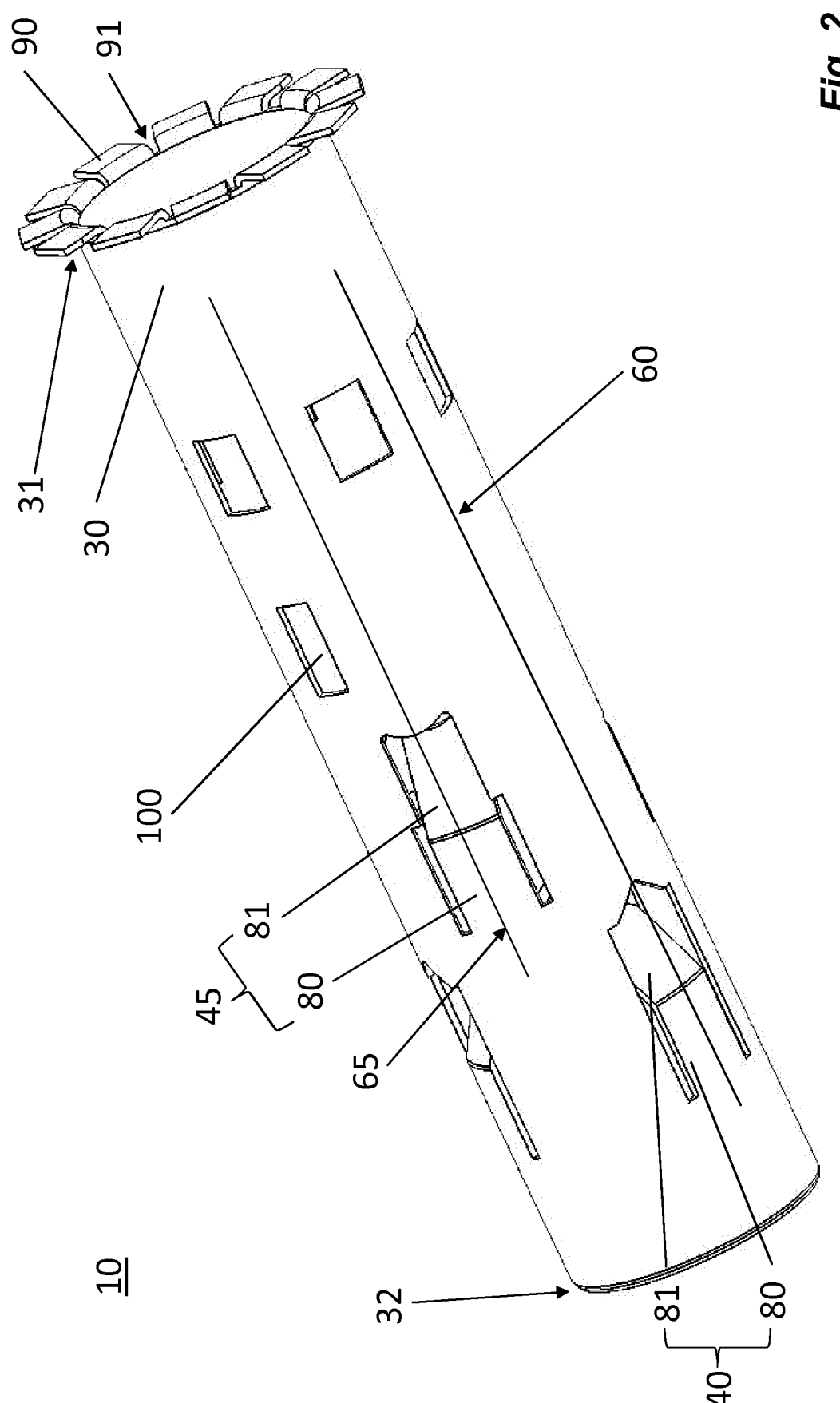
FIG. 2 shows a horizontal view of a needle shield remover according to the first embodiment of the present disclosure.
Figure 3:
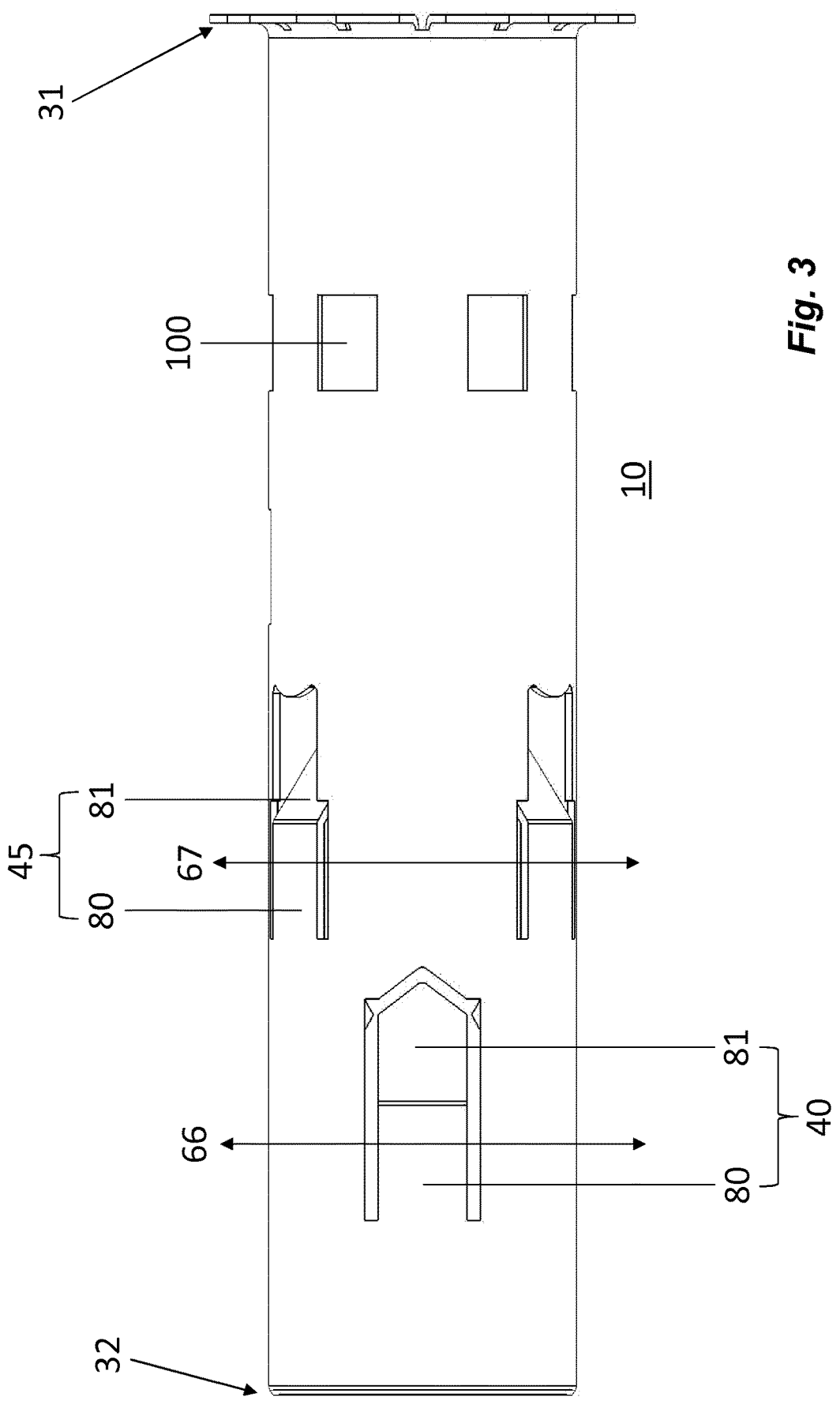
FIG. 3 shows a close-up perspective view of a needle shield remover according to a first embodiment of the present disclosure.

FIG. 2 shows a perspective view of the needle shield remover 10 according to a first embodiment of the present disclosure. FIG. 3 shows a horizontal view of a needle shield remover 10 according to the first embodiment of the present disclosure. Please refer to both FIG. 2 and FIG. 3 for the description that follows. The needle shield remover 10 comprises a longitudinally elongated tubular remover body 30 having a proximal end 31 and a distal end 32. The needle shield remover 10 also includes several first shield gripping members 40 and second shield gripping members 45 disposed on the remover body 30 and configured to make contact with the needle shield on a medicament container (such as syringe) to cover and protect the delivery member (such as needle) attached to the medicament container. The shield gripping members 40, 45 are resilient, extending radially inwardly and towards the proximal end 31. The needle shield remover 10 also includes a plurality of cap fastening members 90 and cut-outs 91 disposed on the proximal end 31 that are configured to couple the needle shield remover 10 with a cap which is then coupled to a medicament delivery device. The interaction between the needle shield remover 10 and the cap will be further explained later in the description below.

Each of the first shield gripping members 40 and second shield gripping members 45 include a first portion 80 and a second portion 81. The first portion 80 extends from the remover body 30 toward the proximal end 31. In other words, one end of the first portion 80 is connected to the remover body 30 while the other end extends towards the proximal end 31. On the other hand, one end of the second portion 81 is connected to the first portion 80 while the other end extends both toward the proximal end 31 and inwardly in order to make contact with the needle shield positioned within the remover body 30. The connection between the first portion 80 and second portion 81 allows the second portion 81 to be flexible with respect to the first portion 80. Similarly, the connection between the first portion 80 and the remover body 30 allows the first portion 80 to be flexible with respect to the remover body 30.

As illustrated in FIG. 2, the first shield gripping members 40 and second shield gripping members 45 are arranged offset in relation to each other both in the longitudinal direction and along the circumference surface of the remover body 30. As illustrated in FIG. 2, the first shield gripping member 40 extends along a first virtual line 60 while the second shield gripping member 45 extends along a second virtual line 65. As illustrated in FIG. 3, the first shield gripping members 40 are distributed around a first circumference 66 while the second shield gripping members 45 are distributed around a second circumference 67. Thus, it can be said that the first shield gripping members 40 and second shield gripping 45 are distributed on the remover body 30 in a zig-zag formation.

The above-mentioned configuration allows the needle shield remover 10 to distribute the gripping forces of shield gripping members 40, 45 to cover a greater surface area of the needle shield. By gripping different sections of the needle shield to spread out the gripping forces, the shield gripping members 40, 45 improve the overall gripping forces applied on the needle shield. This configuration allows the needle shield remover 10 to have greater overall gripping forces on the needle shield without needing to have excessive number of shield gripping members 40, 45 to occupy the entire remover body 30 or have bigger shield gripping members that may prevent the needle shield from being inserted in the needle shield remover 10 during assembly.

Figure 4:
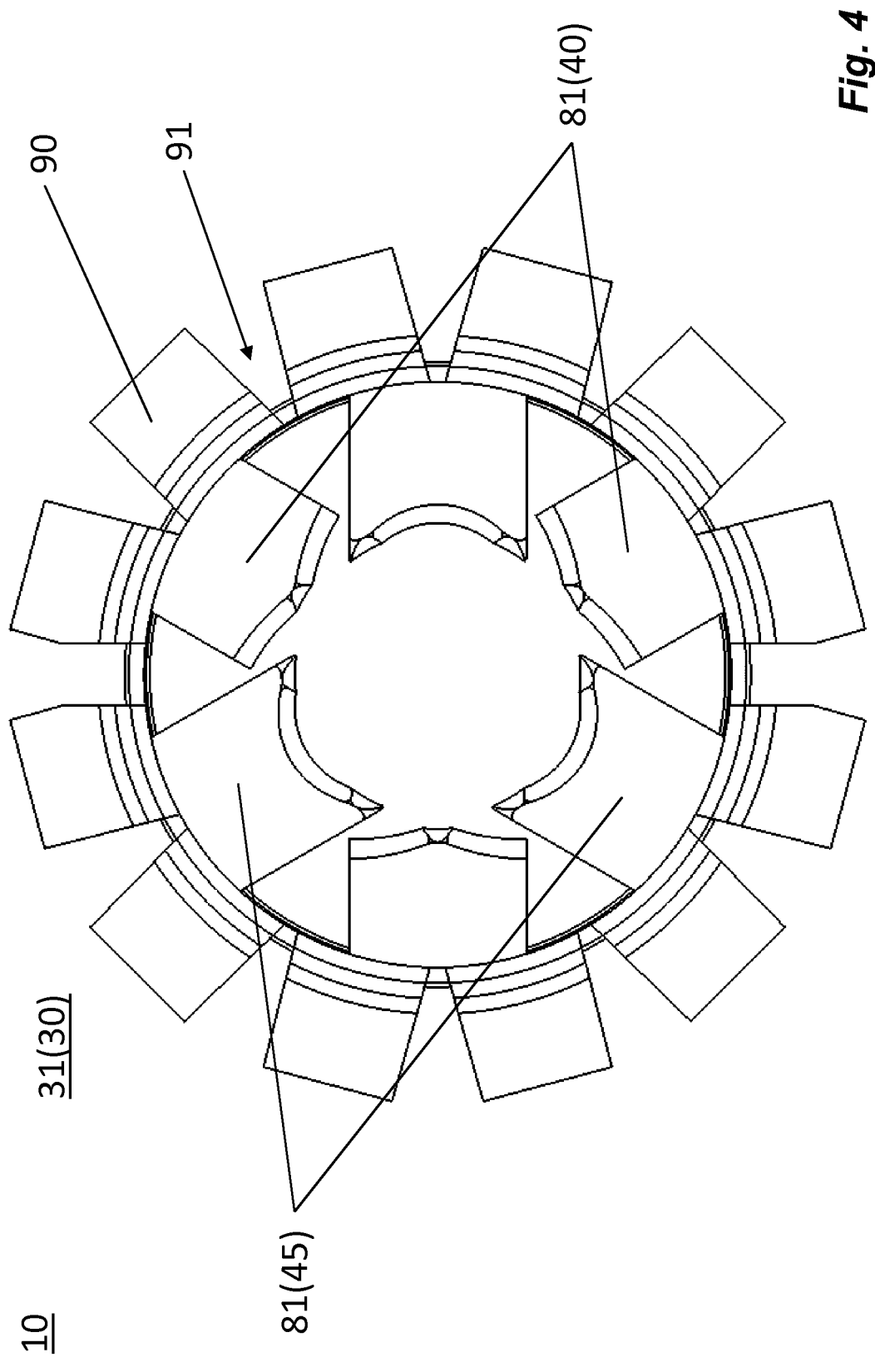
FIG. 4 shows a top perspective view of a needle shield remover according to a first embodiment of the present disclosure.

Here please refer to FIG. 4 that illustrates the top perspective view of the needle shield remover 10. As illustrated, the second portions 81 of the first shield gripping members 40 are configured to have pointed ends while those of the second shield gripping members 45 are configured to have curved ends. The above mentioned shapes of the second portions 81 are designed to create edges that allow the second portions 81 to dig deep into the needle shield during removal when the cap is pulled away from the medicament delivery device. In the present embodiment, the second portions 81 of the first and second shield gripping members 40, 45 are shaped differently, but they are not limited thereto. In other embodiments, the ends of the second shield gripping members 40, 45 can be configured to have substantially identical shape. Further, the second portions may also be configured to be rounded, angled, etc. depending on the gripping force required to grip the needle shield.

Figure 5:
FIG. 5 shows another close-up perspective view of a needle shield remover according to the first embodiment of the present disclosure.

FIG. 5 shows a close up perspective view of a needle shield remover 10 according to a first embodiment of the present disclosure. In the present embodiment, the first shield gripping members 40 and second shield gripping members 45 are configured as cut-outs, or tongues, formed out of a circumferential wall of the remover body 30. Also, each of the first shield gripping members 40 and second shield gripping members 45 includes a first portion 80 and second portion 81. As illustrated in FIG. 5, the needle shield remover 10 includes first openings 82 that accommodate the second portion 81 and allows the second portion 81 to be flexible. Thus, during assembly the second portion 81 can be pushed and flexed outward by the needle shield in order for the needle shield to enter the remover body 30. Further, the needle shield remover 10 includes second openings 83 between the first portion 80 and the remover body 30. In the present embodiment, the second openings 83 are acting as relieve cuts that allows the first portion 80 to be radially flexible both inwardly and outwardly. The second openings 83 thus provides the first portion 80 with the flexibility that reduces the assembly force required to insert the needle shield into the remover body 30.

Figure 6:
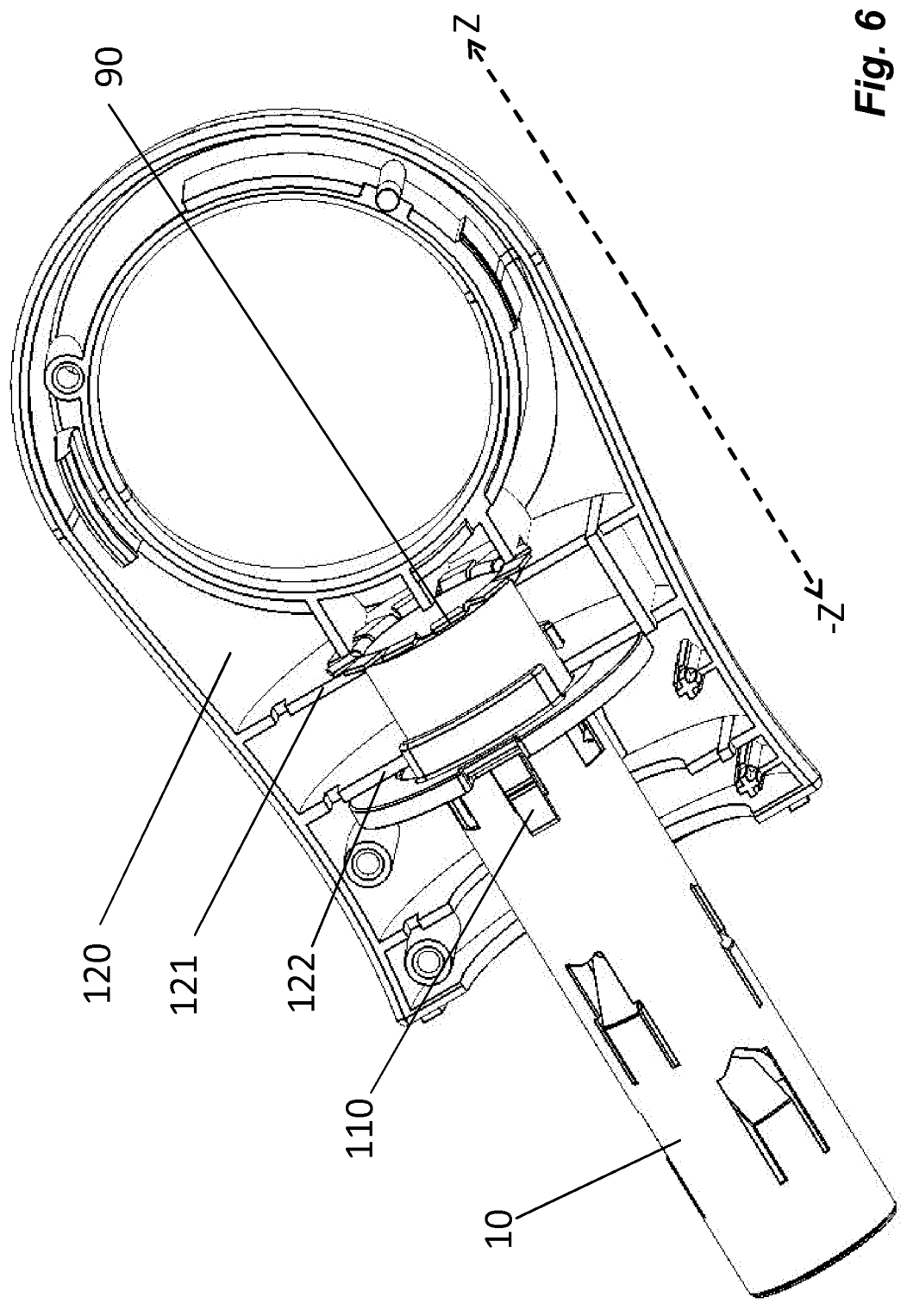
FIG. 6 shows a perspective view of a cap and the needle shield remover according to the first embodiment of the present disclosure.

Please now refer to FIGS. 2 and 6 for the description on coupling between the needle shield remover 10 and the cap 120, wherein one half of the cap 120 is made transparent to facilitate illustration. As illustrated in FIG. 2, cap fastening members 90 and cut-outs 91 extending radially outward from the proximal end 31 of the remover body 30. During assembly, the cap fastening members 90 are disposed on the first assembly layer 121 of the cap 120, wherein the first assembly layer 121 will catch the cap fastening members 90 and prevent the needle shield remover 10 from moving away from the cap 120 in a -Z direction. On the other hand, the cap 120 further includes a cap attachment member 110 coupled with the cap attachment opening 100 (illustrated in FIG. 2) of the needle shield remover 10. The cap attachment member 110 is configured to rest on the second assembly layer 122 of the cap 120. The second assembly layer 122 will catch the cap attachment member 110 and prevent the needle shield remover 10 from moving toward the cap 120 in a Z direction. In summary, the cap fastening members 90 and the cap attachment member 110 not only couple the needle shield remover 10 with the cap 120 but also prevent the needle shield remover 10 from moving axially with respect to the cap 120.

Further, if the needle shield remover 10 is allowed to rotate axially with respect to the cap 120, its shield gripping members 40, 45 may in turn rotate the needle shield which may cause damages to the needle within the needle shield. Thus, to prevent or at least reduce such rotation, the cut-outs 91 are created in order for the cap fastening members 90 to have acute edges for making contact with the inner surface of the cap 120. In such configuration, if a rotational force is exerted on the needle shield remover 10, the edges of the cap fastening members 90 will collide with the inner surface of the cap 120 to cancel out such rotational force and prevent the needle shield remover 10 from rotating. In FIG. 6, a plurality of cap fastening members 90 are formed at the proximal end 31 of the needle shield remover 10 to prevent the needle shield remover 10 from rotating, but it's not limited thereto. In other embodiment, the proximal end 31 can be configured to have extension of other suitable shapes that maintain contact with the inner surface of the cap 120. Also, the cap attachment member 110 in FIG. 6 is separate from the cap 120. However, in other embodiments, the cap attachment member 110 can be an integral part of the cap 120 for coupling with the cap attachment opening 100 (illustrated in FIG. 2) of the needle shield remover 10 and keep the needle shield remover 10 stable.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

The invention claimed is:

1. A needle shield remover for assembly with a cap of a medicament delivery device, wherein the needle shield remover comprises:

a remover body having a circumference surface, proximal end, and a distal end;

a cap attachment structure that includes:

a plurality of cap fastening members extending radially outward at a substantially perpendicular angle from the remover body, wherein the plurality of cap fastening members are arranged to prevent the needle shield remover from moving away from the cap when the cap is coupled with the needle shield remover, wherein a cut-out exists between two neighbouring cap fastening members, and wherein each cut-out creates an acute edge on the respective cap fastening member for making contact with an inner surface of the cap to prevent the needle shield remover from rotating with respect to the cap when the cap is coupled with the needle shield remover, and two or more cap attachment openings on an outer surface of the remover body to be configured to engage a remover attachment member of the cap, wherein the two or more cap attachment openings each comprise an aperture through the remover body;

two or more first shield gripping members; and two or more second shield gripping members;

wherein the two or more first shield gripping members and the two or more second shield gripping members are each configured to engage a needle shield, and wherein each of the two or more first shield gripping members are arranged offset in relation to each of the two or more second shield gripping members both in a longitudinal direction and along a circumference surface of the remover body.

2. The needle shield remover according to claim 1, wherein the remover body is substantially cylindrical and has a first circumference and a second circumference circling around different portions of the remover body, wherein at least one of the two or more first shield gripping members are distributed around the first circumference, and wherein at least one of the two or more second shield gripping members are distributed around the second circumference.

3. The needle shield remover according to claim 1, wherein only one of the two or more first shield gripping members is placed along a first line, and wherein only one of the two or more second shield gripping members is placed along a second line.

4. The needle shield remover according to claim 1, wherein the two or more first shield gripping members and the two or more second shield gripping members each extend radially inwardly and towards the proximal end, and wherein two or more first shield gripping members and the two or more second shield gripping members are configured to engage a circumferential side surface, or the distal end of the needle shield.

5. The needle shield remover according to claim 1, wherein the two or more first shield gripping members and the two or more second shield gripping members have first portions extending from the remover body toward the proximal end and second portions extending radially inward from the first portions and toward the proximal end for engaging the needle shield.

6. The needle shield remover according to claim 5, wherein the second portion of the two or more first shield gripping members has a shape different from that of the second portion of the two or more second shield gripping members.

7. The needle shield remover according to claim 5, wherein the second portion of the two or more first shield gripping members is shaped substantially identical from the second portion of the two or more second shield gripping members.

8. The needle shield remover according to claim 5, wherein the two or more first shield gripping members and the two or more second shield gripping members between the remover body and the first portions, wherein the two or more first shield gripping members and the two or more second shield gripping members have second openings between the remover body and the second portions, wherein the first opening is connected to the second opening, and wherein the first opening allows the first portion to flex radially outward.

9. A medicament delivery device comprising:

a housing; and a cap assembly configured to be mounted to the housing to cover a proximal opening of the housing, the cap assembly includes a cap and a needle shield remover according to claim 1 and configured to be assembled with the cap.

10. The medicament delivery device according to claim 9, wherein the cap assembly includes the remover attachment member of the cap configured to engage the needle shield remover.

11. An assembly comprising:

a cap configured for attachment to a proximal end of a medicament delivery device and comprising a remover attachment; and a needle shield remover axially fixed within the cap, where the needle shield remover comprises:

a remover body having a circumference surface, proximal end and a distal end;

a cap attachment structure that includes:

a plurality of cap fastening members extending radially outward at a substantially perpendicular angle from the remover body, wherein the plurality of cap fastening members are arranged to prevent the needle shield remover from moving away from the cap when the cap is coupled with the needle shield remover, wherein a cut-out exists between two neighbouring cap fastening members, and wherein each cut-out creates an acute edge on the respective cap fastening member for making contact with an inner surface of the cap to prevent the needle shield remover from rotating with respect to the cap when the cap is coupled with the needle shield remover, and two or more cap attachment openings on an outer surface of the remover body to be configured to engage the remover attachment member of the cap, wherein the two or more cap attachment openings each comprise an aperture through the remover body;

two or more first shield gripping members; and two or more second shield gripping members, wherein the two or more first shield gripping members and the two or more second shield gripping members are each configured to engage a needle shield attached to a medicament container positioned within the medicament delivery device, wherein each of the two or more first shield gripping members are arranged offset in relation to each of the two or more second shield gripping members both in a longitudinal direction and along a circumference surface of the remover body, wherein the remover body is substantially cylindrical and has a first circumference and a second circumference circling around different portions of the remover body, where at least one of the two or more first shield gripping members is distributed around the first circumference, and wherein at least one of the two or more second shield gripping members is distributed around the second circumference.

* * * * *